US00PP24224P3

(12) United States Plant Patent
Olesen

(10) Patent No.: US PP24,224 P3
(45) Date of Patent: Feb. 11, 2014

(54) ***ROSA* HYBRID VARIETY DENOMINATION 'POULPAL049'**

(50) Latin Name: ***Rosa* hybrid**
Varietal Denomination: Poulpal049

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 57 days.

(21) Appl. No.: 13/507,011

(22) Filed: May 31, 2012

(65) Prior Publication Data

US 2013/0326756 P1 Dec. 5, 2013

(51) Int. Cl.
*A01H 5/00* (2006.01)

(52) U.S. Cl.
USPC ..... Plt./145

(58) Field of Classification Search
USPC ..... Plt./145
See application file for complete search history.

*Primary Examiner* — Annette Para

(57) ABSTRACT

A new garden rose plant of the compact floribunda class which has abundant, apricot blend flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal049'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 1998 and the resulting seeds were planted in a controlled environment in Fredensborg, Denmark. The new variety, named 'Poulpal049', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant apricot blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal049' from all other varieties of which we are aware.

As part of the rose development program, Mogens N. Olesen germinated the seeds from the aforementioned hybridization during winter of 1998 and conducted evaluations on the resulting seedlings in a controlled environment in Fredensborg, Denmark. 'Poulpal049' was selected in the spring of 1999 by the inventor as a single plant from the progeny of the aforementioned hybridization.

Asexual reproduction of 'Poulpal049' by traditional budding and rooted cuttings was first done by Mogens N. Olesen in the nursery in Fredensborg, Denmark in July, 1999. This initial and other subsequent asexual propagations conducted in controlled environments have demonstrated that the characteristics of 'Poulpal049' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal049'.

Specifically illustrated in the drawing are flowers at various stages of development, flower in parts, leaves, and stems.

DETAILED DESCRIPTION OF THE VARIETY

Figure 1:
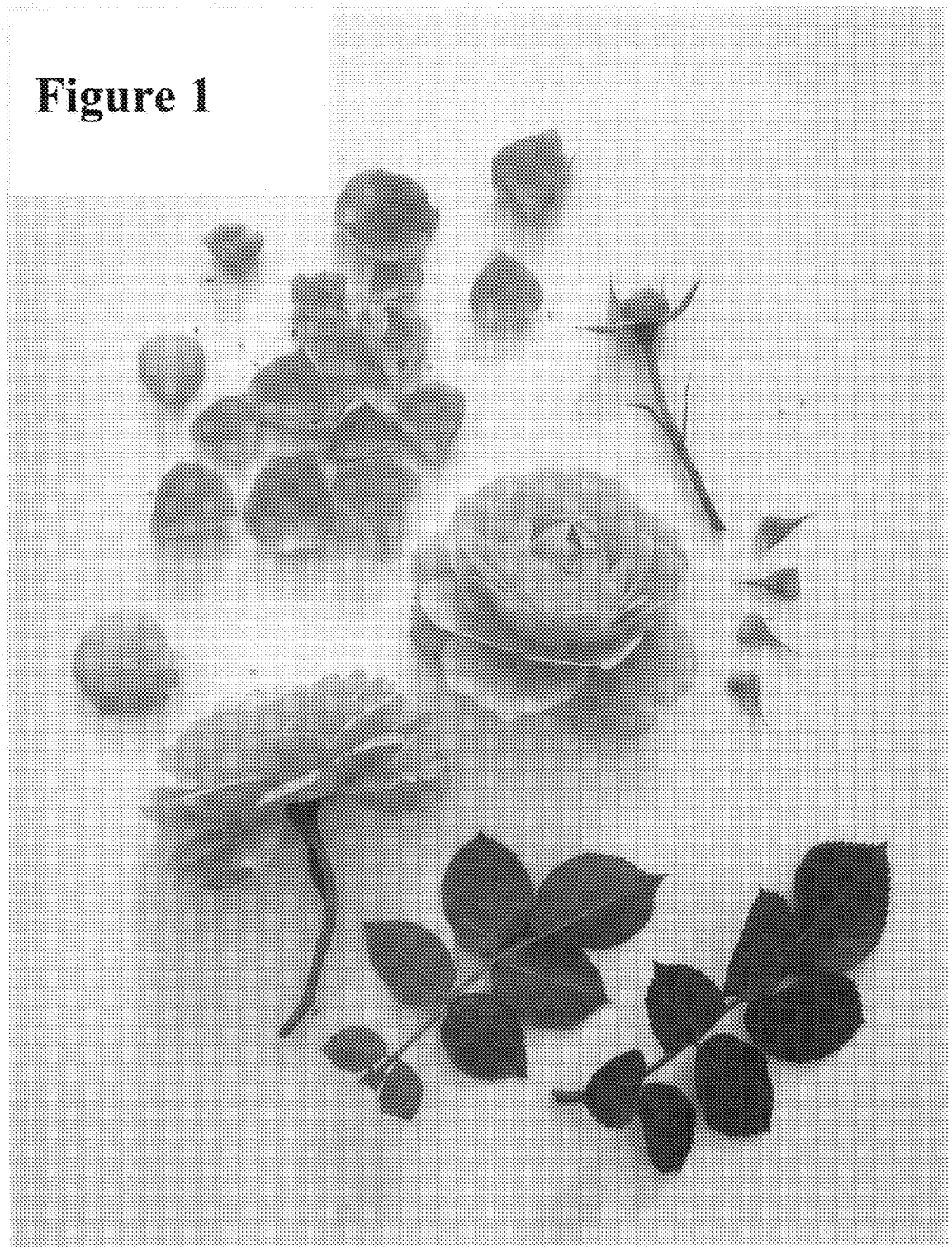
Figure 2:
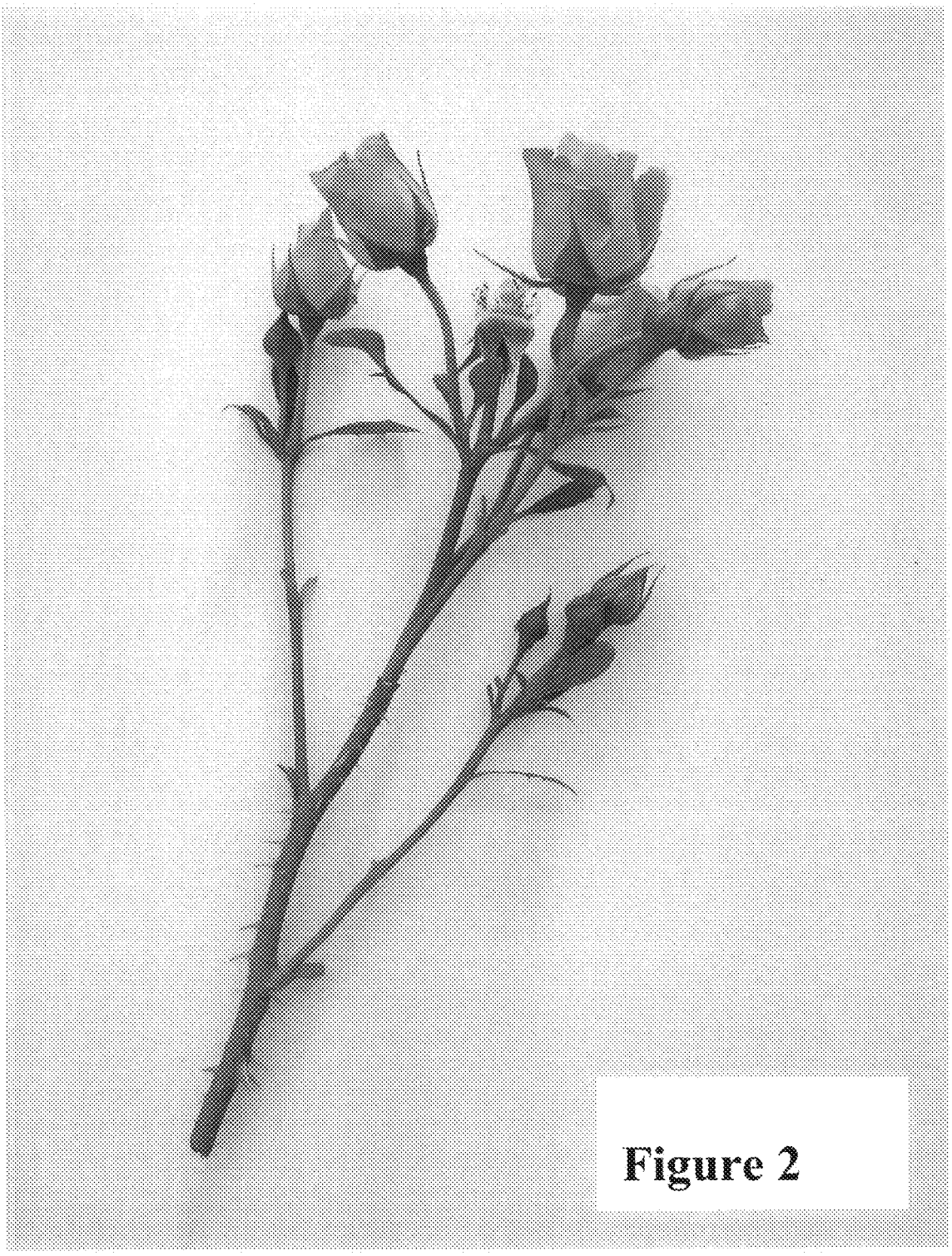

The following is a description of 'Poulpal049',as observed in its growth in in a field nursery in Bakersfield, Calif. 2 years of age, and were grown on their own roots. Color references are made using The Royal Horticultural Society (London, England) Colour Chart, 2001, except where common terms of color are used.

For a comparison, several physical characteristics of the rose variety 'Pouljoey', U.S. Plant Pat. No. 11,598 are compared to 'Poulpal049' in Chart 1.

CHART 1

| | 'Poulpal049' | 'Pouljoey' |
|---|---|---|
| Petal Count | 35 | 55-65 |
| Flower Diameter | 80 mm | 50-60 mm |
| General Tonality of Flower Color | Yellow-Orange Group 21D with intonations of Red Group 37A | Orange-Red Group 31B and Red Group 39B |

Flower and Flower Bud

Blooming habit: Continuous.
Flower bud:

*Size.*—Upon opening, 25 mm in length from base of receptacle to end of bud. Bud diameter is 14 mm.

*Bud form.*—Urceolate.

*Bud color.*—As sepals divide petals are Yellow-Orange Group 15B with intonations of Red Group 42C.

*Sepal inner surface.*—Color: Yellow-Green Group 144C. Surface: Smooth.

*Sepal outer surface.*—Color: Yellow-Green Group 144A. Texture: Somewhat rough abundant with fragrant stipitate glands.

*Sepal shape.*—Apex: Cirrhose. Base: Flat at union with receptacle.

*Sepal margin.*—Margins have weak foliaceous appendages on three of the five sepals.

*Sepal size.*—20 mm long by 10 mm wide.

*Receptacle.*—Texture: Smooth. Size: 7 mm in height by 6 mm wide. Color: Yellow-Green Group 144A. Shape: Campanulate.

*Pedicel.*—Surface: Somewhat rough with many stipitate glands. Length: 25 to 45 mm. Diameter: 2 mm on average. Color: Yellow-Green Group 144A. Strength: Moderate.

*Peduncle.*—Length: 20 to 80 mm. Diameter: 3 mm. Color: Yellow-Green Group 145A.

Flower bud development: Flower buds are borne in clusters of 1 to 3 flower buds per stem, resembling a panicle.

Flower bloom:

*Fragrance.*—Moderate honey perfume.

*Duration.*—The blooms have a duration on the plant of approximately 14 days. Petals fall cleanly away from plant after flowers have fully matured.

*Size.*—Flower diameter is 80 mm when open. Flower depth is 30 mm.

*Flower shape.*—General shape is a rosette with many slightly overlapping petals of different sizes.

*Shape of flower, side view.*—The upper portion is flat. The lower portion is flat.

*Petalage.*—Under normal conditions, flowers have 35 petals total, 7 of which are petaloids.

*General tonality of flower.*—Open flowers are Yellow-Orange Group 21D with intonations of Red Group 37A. Tonality changes to Yellow-Orange Group 18B as the flower ages.

Petal color:

*Upon opening, outer petals.*—Upper surface: Yellow-Orange Group 14D splashed with Red Group 39B. Lower surface: Yellow-Orange Group 16D shaded with Red Group 39B.

*Upon opening, inner petals.*—Upper surface: Yellow Group 11A and 11B splashed with intonations of Orange Group 25C. Lower surface: Yellow Group 9C.

*Basal petal spots.*—Upper surface: Yellow Group 9A. Lower surface: Yellow Group 9A.

*After opening, outer petals and inner petals.*—Upper & lower surface: Yellow Group 11B splashed with Orange Group 25C at middle zone, and Yellow Group 12B at the base.

Petals:

*Petal reflex.*—Not reflexed.

*Margin.*—Entire and uniform. Occasionally a cleft at the margin center. Weak undulations of margin observed.

*Shape.*—Generally narrow elliptic. Apex shape: Rounded. Base shape: Acute.

*Size.*—35 mm (l)×40 mm (w).

*Texture.*—Smooth.

*Thickness.*—Average.

Petaloids:

*Size.*—20 mm (l) by 10 mm (w).

*Quantity.*—Normally 7.

*Shape.*—Irregular and asymmetric. The base is acute and the apex is rounded.

*Color.*—Upper side is Yellow Group 11A and 11B splashed with intonations of Orange Group 25C. Lower surface is Yellow Group 9C.

Reproductive organs:

*Pollen.*—None observed.

*Anthers.*—Size: 1 mm in length. Color: Orange Group 26A. Quantity: 85 on average.

*Filaments.*—Color: Yellow Group 14B. Length: 8 mm.

*Pistils.*—Length: 6 mm. Quantity: 60 on average.

*Stigmas.*—Color: Yellow Group 160A.

*Styles.*—Color: Greyed-Yellow Group 160C.

*Location of stigmas.*—Inferior in location relative to the length of the filaments and the height of the anthers.

*Hips.*—None Observed.

Plant

Plant growth: Upright, bushy. Plants are 50 cm in height, and 50 cm wide.

Stems:

*Color.*—Juvenile growth: Yellow-Green Group 144A. Mature growth: Yellow-Green Group 144A.

*Length.*—On average, canes are 35 cm from the base of the plant to the flowering portion.

*Diameter.*—4 mm.

*Internodes.*—On mature canes, there is an average distance of 40 mm between nodes.

*Surface texture.*—Young wood: Rough. Many small prickles. Older wood: Rough. Many small prickles.

Long prickles:

*Incidence.*—20 prickles per 10 cm of stem.

*Size.*—Average length of prickles on mature stems is 9 mm.

*Shape.*—Upper portion is linear. Lower portion is concave.

*Color.*—Juvenile prickles: Yellow-Green Group 154C. Mature prickles: Greyed-Orange Group N170C.

Plant foliage:

*Compound leaf.*—120 mm (l)×60 (w).

*Quantity.*—2 leaves per 10 cm of stem on average.

*Leaf bearing angle to the stem.*—90 degrees.

*Color of juvenile foliage.*—Upper side: Yellow-Green Group 144A. Lower side: Yellow-Green Group 144B.

*Color of mature foliage.*—Upper side: Yellow-Green Group 146A. Lower side: Yellow-Green Group 146B.

Plant leaves and leaflets:

*Stipules.*—Size: 12 mm in length. Quantity: 2 per compound leaf. Shape: Linear, slightly broad based with outward extending apecies. Margins: Finely serrated with few stipitate glands. Color: Yellow-Green Group 144A.

*Petiole.*—Length: 20 mm. Diameter: 2 mm.

*Upper surface.*—Color: Yellow-Green Group 144A.

*Lower surface.*—Color: Yellow-Green Group 144B.

*Rachis.*—Length: 50 mm. Upper surface: Yellow-Green Group 144A. Lower surface: Yellow-Green Group 144B.

Leaflet:

*Quantity.*—Normal number of leaflets leaves in middle of the stem is 7 leaflets.

*Margins.*—Serrated.

*Size.*—Average size of the terminal leaflet on normal leaves is 50 mm in length by 31 mm wide.

*Shape.*—Generally ovate. Base: Rounded. Apex: Cuspidate.

*Texture.*—Smooth.

*Thickness.*—Average.

*Arrangement.*—Odd pinnate.

*Venation.*—Reticulate.

*Glossiness.*—Moderately glossy.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

It is claimed:

1. A new and distinct variety of rose plant of the compact floribunda rose class named 'Poulpal049', substantially as illustrated and described herein, due to its abundant apricot blend flowers, disease resistance, and extended period of bloom.

* * * * *